US011402393B2

(12) United States Patent
Struck et al.

(10) Patent No.: US 11,402,393 B2
(45) Date of Patent: Aug. 2, 2022

(54) PROCALCITONIN FOR THE DIAGNOSIS OF BACTERIAL INFECTIONS AND GUIDANCE OF ANTIBIOTIC TREATMENT IN PATIENTS WITH NON-SPECIFIC COMPLAINTS

(71) Applicant: B.R.A.H.M.S GMBH, Hennigsdorf (DE)

(72) Inventors: Joachim Struck, Berlin (DE); Christian Nickel, Basel (CH); Roland Bingisser, Basel (CH); Sven Giersdorf, Berlin (DE); Oliver Hartmann, Berlin (DE)

(73) Assignee: B.R.A.H.M.S GMBH, Hennigsdorf (DE)

(*) Notice: Subject to any disclaimer, the term of this patent is extended or adjusted under 35 U.S.C. 154(b) by 518 days.

(21) Appl. No.: 15/700,531

(22) Filed: Sep. 11, 2017

(65) Prior Publication Data

US 2017/0370949 A1    Dec. 28, 2017

Related U.S. Application Data

(63) Continuation of application No. 13/583,350, filed as application No. PCT/EP2011/053476 on Mar. 8, 2011, now abandoned.

(30) Foreign Application Priority Data

Mar. 8, 2010 (EP) .................................... 10002363

(51) Int. Cl.
*G01N 33/74* (2006.01)
*G01N 33/569* (2006.01)

(52) U.S. Cl.
CPC ....... *G01N 33/74* (2013.01); *G01N 33/56911* (2013.01); *G01N 2333/585* (2013.01); *G01N 2800/52* (2013.01)

(58) Field of Classification Search
CPC ............. G01N 33/74; G01N 33/56911; G01N 2333/585; G01N 2800/52
See application file for complete search history.

(56) References Cited

U.S. PATENT DOCUMENTS

2011/0136161 A1   6/2011   Struck et al.
2011/0152170 A1   6/2011   Struck et al.

FOREIGN PATENT DOCUMENTS

WO      2009/019230 A2      2/2009
WO      WO-2009019230 A2 *  2/2009  ............. G01N 33/74

OTHER PUBLICATIONS

The Merck Manual (Sepsis and Septic Shock, 2008, 7 pages). (Year: 2008).*
https://www.mayoclinic.org/diseases-conditions/infectious-diseases/symptoms-causes/syc-20351173, downloaded Feb. 22, 2020, PDF provided (Year: 2020).*
https://www.healthline.com/health/signs-of-infection#signs-of-infection, downloaded Feb. 22, 2020, PDF provided (Year: 2020).*
Nemec et al., Acad. Emerg. Med., 2010;17:284-292 (Year: 2010).*
Definition of "anorexia" from https://www.merriam-webster.com/dictionary/anorexia, screen shot provided, accessed from the internet online on Aug. 31, 2020. (Year: 2020).*
Chan et al., Critical Care Feb. 2004 vol. 8 No. 1, R12-R20 (Year: 2004).*
Mouton, Am Fam Physician 2001;63:257-68 (Year: 2001).*
Guven et al., American Journal of Emergency Medicine, vol. 20, No. 3, pp. 202-206, May 2002 (Year: 2002).*
*Warner-Jenkinson* v. *Hilton Davis*, 520 US 17, 41 USPQ2d 1865, 117 S. Ct 1040 (1997) (Year: 1997).*
Definition of "indicate" obtained from the internet on Apr. 10, 2021 at https://www.merriam-webster.com/dictionary/indicate (Year: 2021).*
Judy Foreman boston.com 2008 article obtained from the internet per a Google search on Sep. 11, 2021, one page (Year: 2008).*
Schneider and Lam, Pathology (Aug. 2007) 39(4), pp. 383-390 (Year: 2007).*
Aminov, Frontiers in Biology, Dec. 2010, vol. 1, Article 134, 7 pages (Year: 2010).*
Schneider and Lam, Pathology, Aug. 2007, 39(4)383-390 (Year: 2007).*
Caterino et al., Acad Emerg Med d Apr. 2004, vol. 11, No. 4, 393-396 (Year: 2004).*
510(k) documents for B'R'A'H'M'S PCT sensitive KRYPTOR® Test System, Mar. 2008 (Year: 2008).*
Povoa, Intensive Care Med (2002) 28:235-243 (Year: 2002).*
Summah, H., et al., "Biomarkers: A Definite Plus in Pneumonia," Mediators of Inflammation, 2009, vol. 2009; Article ID 675753, pp. 1-9, Hindawi Publishing Corporation; Cited in International Search Report, dated Apr. 27, 2011, issued in corresponding PCT/EP2011/053476.
Briel, M., et al., "Procalcitonin-guided antibiotic use versus a standard approach for acute respiratory tract infections in primary care: study protocol for a randomised controlled trial and baseline characteristics of participating general practitioners [ISRCTN73182671]," BMC Family Practice, Biomed Central, London, GB LKND-, Aug. 18, 2005, vol. 6, No. 1, pp. 1-8; Cited in International Search Report, dated Apr. 27, 2011, issued in corresponding PCT/EP2011/053476.
Robinson, D. T., et al., "Neonatal Sepsis in the Emergency Department," Clinical Pediatric Emergency Medicine, W. B. Saunders LNKD-, Sep. 1, 2008, vol. 9, No. 3, pp. 160-168, Elsevier Inc.; Cited in International Search Report, dated Apr. 27, 2011, issued in corresponding PCT/EP2011/053476.
International Search Report, dated Apr. 27, 2011, issued in corresponding PCT/EP2011/053476.
Written Opinion, dated Apr. 27, 2011, issued in corresponding PCT/EP2011/053476.
The Merck Manual Home Health Handbook. "Bacteremia, Sepsis, and Septic Shock", 2008.
Bone et al., Chest, vol. 101, pp. 1644-1655, 1992.

(Continued)

*Primary Examiner* — Larry D Riggs, II
*Assistant Examiner* — Joseph Fischer
(74) *Attorney, Agent, or Firm* — Millen, White, Zelano & Branigan, PC; Ryan Pool (57) ABSTRACT

The present invention relates to the determination of the level of marker peptides in a sample derived from a bodily fluid of a subject presenting with non-specific complaints.

6 Claims, 4 Drawing Sheets
Specification includes a Sequence Listing.

(56) References Cited

OTHER PUBLICATIONS

Riedel; "Procalcitonin as a Marker for the Detection of Bacteremia and Sepsis in the Emergency Deparlmnent" Am J Clin Pathol 2011;135:182-189.
Nemec: "Patients Presenting to the Emergency Deparlmnent With Non-specific Complaints: The Basel Non-specific Complaints (BANC) Study" Acad Emerg Med • Mar. 2010, vol. 17, No. 3 , pp. 284-292.

* cited by examiner

Table 1: Sensitivities and Specificities (in %) for different PCT cut-off values for patients who presented to the ED with non-specific complaints

| PCT cut-off [ng/mL] | Sensitivity (in %) | Specificity (in %) |
|---|---|---|
| 0.03 | 89.5 | 36.5 |
| 0.05 | 77.9 | 58.7 |
| 0.10 | 54.7 | 73.9 |
| 0.20 | 38.4 | 83.9 |
| 0.25 | 33.7 | 88.2 |
| 0.50 | 16.3 | 93.3 |

SEQUENCE LISTING

```
<160> NUMBER OF SEQ ID NOS: 1

<210> SEQ ID NO 1
<211> LENGTH: 116
<212> TYPE: PRT
<213> ORGANISM: Homo sapiens

<400> SEQUENCE: 1

Ala Pro Phe Arg Ser Ala Leu Glu Ser Ser Pro Ala Asp Pro Ala Thr
1               5                   10                  15

Leu Ser Glu Asp Glu Ala Arg Leu Leu Leu Ala Ala Leu Val Gln Asp
            20                  25                  30

Tyr Val Gln Met Lys Ala Ser Glu Leu Glu Gln Glu Gln Glu Arg Glu
        35                  40                  45

Gly Ser Ser Leu Asp Ser Pro Arg Ser Lys Arg Cys Gly Asn Leu Ser
    50                  55                  60

Thr Cys Met Leu Gly Thr Tyr Thr Gln Asp Phe Asn Lys Phe His Thr
65                  70                  75                  80

Phe Pro Gln Thr Ala Ile Gly Val Gly Ala Pro Gly Lys Lys Arg Asp
                85                  90                  95

Met Ser Ser Asp Leu Glu Arg Asp His Arg Pro His Val Ser Met Pro
            100                 105                 110

Gln Asn Ala Asn
        115
```

PROCALCITONIN FOR THE DIAGNOSIS OF BACTERIAL INFECTIONS AND GUIDANCE OF ANTIBIOTIC TREATMENT IN PATIENTS WITH NON-SPECIFIC COMPLAINTS

The instant application contains a Sequence Listing which has been submitted in ASCII format via EFS-Web and is hereby incorporated by reference in its entirety. Said ASCII copy, created on Sep. 7, 2012, is named BOEHMERP0160SQL.txt and is 1,407 bytes in size.

FIELD OF THE INVENTION

The present invention is in the field of clinical diagnostics. Particularly the present invention relates to the determination of Procalcitonin (PCT) in a sample derived from a bodily fluid of a subject with non-specific complaints.

BACKGROUND OF THE INVENTION

Patients presenting with non-specific complaints (NSC) are a well-known but poorly defined population. This is frequently seen for instance in emergency departments (ED). Affected individuals often complain of "not feeling well", "feeling weak", "feeling exhausted", "being tired or sleepy", feeling "dizzy", complain of being unable to cope with usual daily activities, have a lack of appetite (van Bokhoven et al. 2008. *J Clin Epidemiol;* 61:318-22). Some patients may fail to recall why they were sent to the ED. During the care of NSC patients, ED physicians face a broad differential diagnosis ranging from insufficient home care to acute life-threatening conditions (Gordon 1986. *Geriatrics* 41(4): 75-80). Patients with NSC are among the most challenging to ED physicians (Chew and Birnbaumer 1999. *Emerg Med Clin North Am* 17(1):265-78). Moreover, the clinical picture is often blurred by factors such as co-morbidities, poly-pharmacy or altered mental state.

Vanapee et al. demonstrated that up to 20% of older individuals presenting to the ED have no specific complaints (Vanpee et al. 2001. *Eur J Emerg Med* 8(4):301-4). Furthermore, 50% of older individuals without specific complaints suffered from an acute medical problem (Rutschmann et al. 2005. *Swiss Med Wkly* 135(9-10):145-50).

Procalcitonin (PCT) has become a well-established biomarker for the diagnosis of sepsis. PCT reflects the severity of a bacterial infection and is in particular used to monitor progression of infection into sepsis, severe sepsis, or septic shock. It is possible to use PCT to measure the activity of the infection-associated systemic inflammatory response, to control success of antibacterial therapy, and to estimate prognosis (Assicot et al. 1993. *Lancet* 341:515-8; Clec'h C et al. 2004. *Crit Care Med* 32:1166-9; Lee et al. 2004. *Yonsei Med J* 45:29-37; Meisner et al. 2005. *Curr Opin Crit Care* 11:473-480; Wunder et al. 2004. *Inflamm Res* 53: 158-163). The increase of PCT levels in patients with sepsis correlates with mortality (Oberhoffer et al. 1999. *Clin Chem Lab Med* 37:363-368).

PCT has already been used for therapy guidance of antibiotics in patients with symptoms of infections (e.g. shortness of breath, fever). In patients presenting at the ED with symptoms of lower respiratory tract infections, PCT was measured and only patients with PCT concentrations >0.25 ng/mL or >0.5 ng/mL were treated with antibiotics (Christ-Crain et al. 2004. *Lancet* 363:600-7). In patients with community-acquired pneumonia (CAP) antibiotic treatment was based on serum PCT concentrations (strongly discouraged at PCT concentrations <0.1 ng/mL; discouraged at PCT concentrations <0.25 ng/mL; encouraged at PCT concentrations >0.25 ng/mL, and strongly encouraged at PCT concentrations >0.5 ng/mL) (Christ-Crain et al. 2006. *Am J Resp Crit Care Med* 174:84-93). PCT guidance substantially reduced antibiotic use in CAP without deterioration of patients outcome. Similarly, PCT-guided therapy using the same decision thresholds as described above, also markedly reduced antibiotic use for acute respiratory tract infections in primary care without compromising patients outcome (Briel et al. 2008. *Arch Intern Med* 168:2000-7; Burkhardt et al. 2010. *Eur Resp J Express; doi:* 10.1183/09031936.00163309).

The use of PCT measurement for the diagnosis of prevalent bacterial infections has so far been limited to patients, who due to the symptoms they were presenting with were already suspected to suffer from a bacterial infection. It is totally unclear so far, whether such use of PCT may be possible also in patients presenting with non-specific complaints, which do not point directly to a bacterial infection being the possible reason for these complaints. In such patients the prevalence of bacterial infections is not known, and it might be relatively low. It is highly challenging and not at all obvious that a biomarker such as PCT might be able to identify in such patient group those patients with bacterial infections with a meaningful sensitivity and specificity, since the other patients without bacterial infections are many, they are definitely sick, they might be very sick. So far PCT determination has been conducted in patients with suspect of having a bacterial infection because said patients showed symptoms or presented complaints that were pointing to a bacterial infection. It has never been practiced to measure the PCT level with the intention to diagnose a prevalent bacterial infection in a patient having non-specific complaints.

A diagnostic method to determine the etiology of inflammatory processes by determining the concentration of PCT and to ascertain from the presence or absence of the peptide whether the inflammation is of infectious or non-infectious etiology is described in EP 0 80 702 B1.

It was surprisingly found that the measurement of Procalcitonin levels in a sample of a bodily fluid from a patient presenting with non-specific complaints could be used for the diagnosis and treatment guidance of bacterial infection in these patients.

SUMMARY OF THE INVENTION

The invention relates to a method for diagnosing or identifying a bacterial infection in a patient who presented to the emergency department with non-specific complaints. The method comprises the following steps:
  (i) providing a sample from a patient presenting with non-specific complaints;
  (ii) determining the level of Procalcitonin (PCT) or a fragment thereof of at least 12 amino acids in length, preferably more than 50 amino acids in length, more preferably more than 110 amino acids in length, in said sample; and
  (iii) determining whether said patient has a bacterial infection or not by comparing said determined PCT level with a predetermined threshold level.

The invention further relates to the use of such a method for providing treatment guidance for the administration of an antibiotic to a patient who presented with non-specific complaints and for monitoring the antibiotic therapy.

BRIEF DESCRIPTION OF THE DRAWINGS

FIG. 4.

DETAILED DESCRIPTION OF THE INVENTION

The invention relates to a method for diagnosing or identifying a bacterial infection in a patient who presented with non-specific complaints. The method comprises the following steps:
  (i) providing a sample from a patient presenting with non-specific complaints;
  (ii) determining the level of Procalcitonin (PCT) or a fragment thereof of at least 12 amino acids in length, preferably more than 50 amino acids in length, more preferably more than 110 amino acids in length, in said sample; and
  (iii) determining whether said patient has a bacterial infection or not by comparing said determined PCT level with a predetermined threshold level.

In one embodiment of the invention the bacterial infection is asymptomatic (e.g. a bacterial infection that has not yet shown clinical symptoms but being present) in a patient who presented with non-specific complaints.

Non-Specific complaints are not restricted to the group but may be selected from the group comprising complains of "not feeling well", "feeling weak", "feeling exhausted", "being tired or sleepy", feeling "dizzy", have a lack of appetite or simply complain of being unable to cope with usual daily activities or patients may fail to recall why they were sent to the ED.

A specific complaint usually provides key information and allows generating a working diagnosis or following a predefined diagnostic protocol. Specific complaints are well-recognized as such in the literature and diagnostic protocols are often applied (Siegenthaler W. *Differential Diagnosis in Internal Medicine: From Symptom to Diagnosis*. New York: Thieme Medical Publishers; 2007).

Among specific complaints there are complaints, where infections, especially bacterial infections are commonly considered as being the reason for the complaints. These specific complaints vary depending on the type of bacterium and the location of the bacterial infection. Such specific complaints are not restricted to the group but may be selected from the group comprising complains of headaches, pain that is in a specific part of the body (e.g. the abdomen), fever (>38° C.), a respiratory symptom selected from the group comprising cough, sputum production, dyspnea, tachypnea and pleuritic pain; one finding during auscultation (e.g. rales, crepitation) and one sign of infection (core body temperature >38° C., shivering) and one sign of digestive tract infection (nausea, vomiting, diarrhea).

Further Specific Complaints are Outlined Below:
The classic symptoms of a bacterial infection are localized redness, heat, swelling and pain. One of the hallmarks of a bacterial infection is local pain, pain that is in a specific part of the body. For example, if a cut occurs and it is infected with bacteria, pain will occur at the site of the infection. Bacterial throat pain is often characterized by more pain on one side of the throat. An ear infection is more likely to be bacterial if the pain occurs in only one ear.

As stated above, bacterial infection symptoms differ with the type of infections. Depending on the infected area, the symptoms may vary. However, symptoms are always experienced, also when the area is infected even slightly. When bacterial infections are found in respiratory tract, symptoms related to throat and respiration are found. Throat infection is very common in people living in areas with high pollution. Pneumonia is very common in children and elderly people for whom natural immune power will be very less. Sinusitis and pharyngitis are also found in people who suffer from bacterial infections. Colored nasal discharge and headaches are commonly experienced when bacterial infections are in the respiratory tract.

When infections are found in the digestive tract (e.g. gastroenteritis), symptoms are mostly related to digestion problems. Inflammation and pain in the stomach are normally experienced. Diarrhea and vomiting are other symptoms that indicate infections in gastrointestinal tract. Nausea and dehydration may also be experienced as a result of severe bacterial infection symptoms.

Foul or fishy smell in the vaginal area is a symptom for vaginal infections. Vagina in women has several types of bacteria that do good for the organ. However, if the production of this type of bacteria is irregular, it may lead to infection. Bacterial infection symptoms for infections in urinary tract include itching and pain the urinals. Vaginal infection and infections in urinary tract should not be ignored as they may cause further inflammation in the internal organs.

Meningitis is a serious consequence of bacterial infections in the membranes that cover brain and spinal chord. Though this can be found in adults also, infants are more susceptible to this problem. Common bacterial infection symptoms for meningitis are stiffness in body and neck, headache, irritability, fever or lower than normal temperature, and skin rashes.

Most dangerous bacterial infections lead to sepsis, a critical condition which leads to malfunctioning of organs causing death. Fever and heavy shaking in the body are the bacterial infection symptoms for sepsis. Pains in joints are also felt by patients with sepsis. This has to be treated immediately to stop the infection from spreading to internal organs. In case of sepsis, the patient will be admitted in the hospital for intensive treatment.

Erysipelas is an acute bacterial infection of the dermis, resulting in inflammation. Patients typically develop symptoms including high fevers, shaking, chills headaches, vomiting, and within 48 hours of the initial infection. The erythematous skin lesion enlarges rapidly and has a sharply demarcated raised edge. It appears as a red, swollen, warm, hardened and painful rash, similar in consistency to an orange peel. More severe infections can result in vesicles, bullae, and petechiae, with possible skin necrosis. Lymph nodes may be swollen, and lymphedema may occur. Occasionally, a red streak extending to the lymph node can be seen. The infection may occur on any part of the skin including the face, arms, fingers, legs and toes, but it tends to favor the extremities. Fat tissue is most susceptible to infection, and facial areas typically around the eyes, ears, and cheeks.

Peritonitis is an inflammation of the peritoneum, the serous membrane which lines part of the abdominal cavity and viscera. Peritonitis may be localized or generalized, and may result from infection (often due to rupture of a hollow organ as may occur in abdominal trauma or appendicitis). The main manifestations of peritonitis are acute abdominal pain, abdominal tenderness, and abdominal guarding. The localization of these manifestations depends on whether peritonitis is localized (e.g. appendicitis or diverticulitis before perforation), or generalized to the whole abdomen. In either case pain typically starts as a generalized abdominal pain (with involvement of poorly localizing innervation of the visceral peritoneal layer), and may become localized later (with the involvement of the somatically innervated parietal peritoneal layer). Perforation of a part of the gastrointestinal tract and disruption of the peritoneum are the most common causes of infected peritonitis.

Cholangitis is an inflammation of the bile duct. The most common cause is a bacterial infection. The classic triad of cholangitis is fever, jaundice, and right upper quadrant abdominal pain.

Cholecystitis is an inflammation of the gall bladder and usually presents as a pain in the right upper quadrant. This is usually accompanied by a low grade fever, vomiting and nausea.

Osteomyelitis means an infection of the bone or bone marrow. In general, microorganisms may infect bone through one or more of three basic methods: via the bloodstream, contiguously from local areas of infection, or penetrating trauma, including iatrogenic causes such as joint replacements or internal fixation of fractures or root-canaled teeth. Signs and symptoms of an osteomyelitis include fever, pain in the area of the infection, swelling, warmth and redness over the area of the infection. http://en.wikipedia.org/wiki/Infection:

The classification of "non-specific" complaints implies the subjective judgement of the ED physician. Such judgement depends on physician-related factors such as clinical experience and skills, and on weighting the different complaints which may guide further assessment. Patient-related factors include the ability to verbalize complaints or the patient's cognitive state. As a general scope, a definition of NSC aims to narrow subjectivity in the classification of patients and, as a consequence, facilitates structured proactive patient management.

A specific complaint usually provides key information and allows generating a working diagnosis or following a predefined diagnostic protocol. Specific complaints are well-recognized as such in the literature and diagnostic protocols are often applied (Marx J A, Hockberger R, Walls R. *Rosen's Emergency Medicine: Concepts and Clinical*. Sixth Edition ed. St Louis: Mosby; 2005; Siegenthaler W. *Differential Diagnosis in Internal Medicine: From Symptom to Diagnosis*. New York: Thieme Medical Publishers; 2007).

In contrast to specific complaints, NSC was defined as the entity of all complaints which are not part of the set of specific complaints or signs or where an initial working diagnosis cannot be established. It is preferred to define NSC as the remainder after exclusion of specific complaints, because an active definition may require an almost endless enumeration of possible non-specific complaints. Such a long and complicated definition would likely exclude certain NSC patients because their symptoms failed to exactly match the predefined list. Thus, the NSC list given in this application may not be complete. The term working diagnosis is used in the context of the present NSC definition for situations where patients present with NSC, but a diagnosis is likely nevertheless given the facts and findings at the time of presentation (e.g. a patient who presents with weakness and anaemic pallor).

Figure 3:
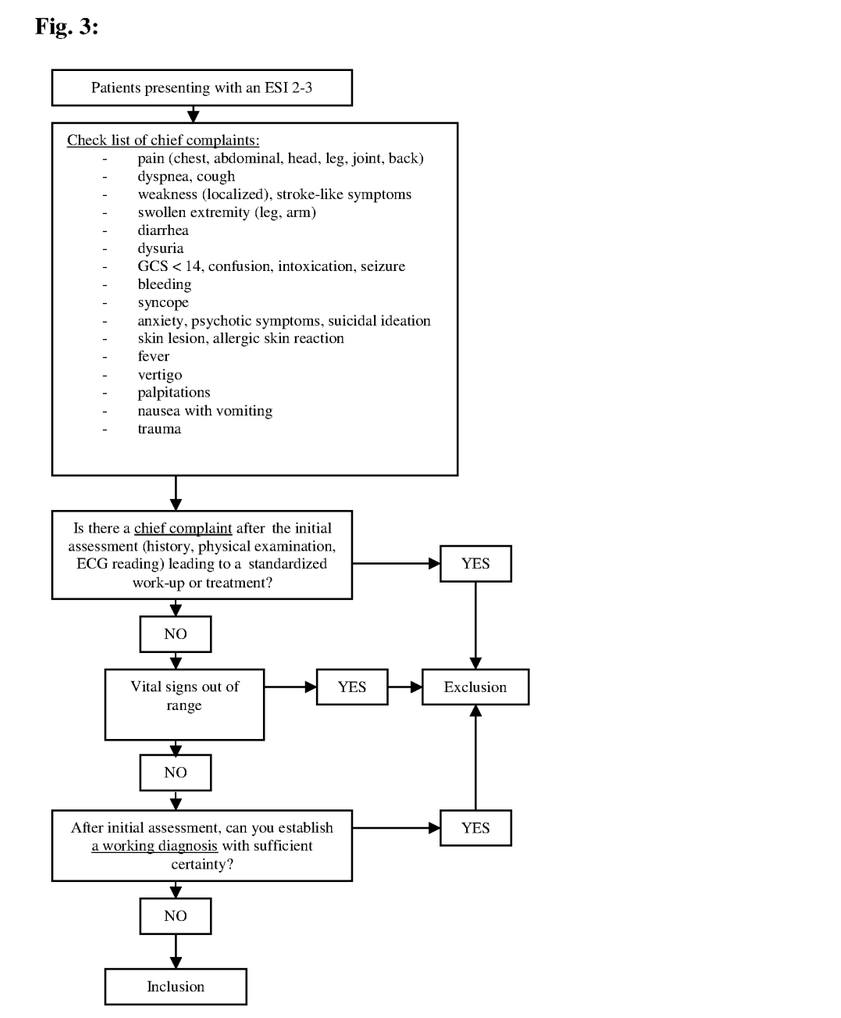
FIG. 3: Identification of patients with non-specific complaints in the BANC study
Figure 4:
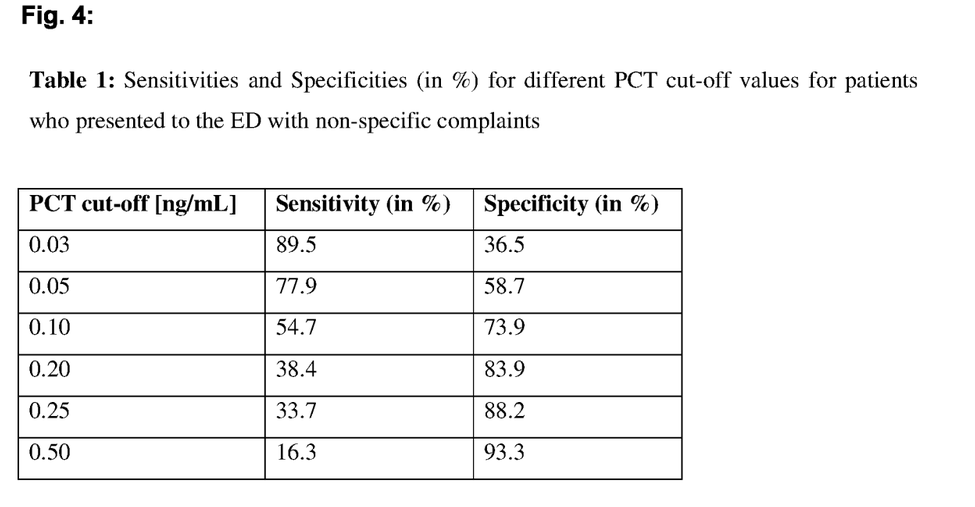
FIG. 4 illustrates Table 1.

FIG. 3 summarizes this definition in a procedural way. In the most preferred embodiment nonspecific complaints are defined as complaints which lead to an inclusion according to FIG. 3. This means that the patient according to the invention does not exhibit one of the following complaints: pain (chest, abdominal, head, leg, joint, back), dyspnea, cough, weakness (localized), stroke-like symptoms, swollen extremity (leg, arm), diarrhea, dysuria, GCS <14, confusion, intoxication, seizure, bleeding, syncope, anxiety, psychotic symptoms, suicidal ideation, skin lesion, allergic skin reaction, fever, vertigo, palpitations, nausea with vomiting, trauma. Furthermore, the question whether there is a chief complaint after the initial assessment (history, physical examination, ECG reading) leading to a standardized work-up or treatment is answered with: no. Further none of the vital signs (body temperature, pulse or heart rate, blood pressure and respiratory rate) are out of range in said patient. Moreover, after initial assessment a working diagnosis cannot be established, especially not with sufficient certainty.

In a very special embodiment of the invention from said patient group having NSC preferably those patients are excluded having a primary disease such primary disease being preferably not an infection and/or being preferably selected from the group comprising arteriosclerosis, heart failure, acute coronary syndrome, coronary disease, myocardial infarction, cancer, diabetes, chronic gastrointestinal diseases, chronic renal diseases, hypertension, orthopaedic diseases including osteoporosis, and neurodegenerative diseases including Alzheimer's disease.

The term "level" in the context of the present invention relates to the concentration (preferably expressed as weight/volume; w/v) of PCT (or a fragment/precursor) in a sample taken from a subject.

The term "patient" as used herein refers to a living human or non-human organism that is receiving medical care or that should receive medical care due to a disease. This includes persons with no defined illness who are being investigated for signs of pathology. Thus, the methods and assays described herein are applicable to both human and veterinary disease.

The term "sample" as used herein refers to a sample of bodily fluid obtained for the purpose of diagnosis, prognosis, or evaluation of a subject of interest, such as a patient. Preferred test samples include blood, serum, plasma, cerebrospinal fluid, urine, saliva, sputum, and pleural effusions. In addition, one of skill in the art would realize that some test samples would be more readily analyzed following a fractionation or purification procedure, for example, separation of whole blood into serum or plasma components.

Thus in a preferred embodiment of the invention the sample is selected from the group consisting of a blood sample, a serum sample, a plasma sample, a cerebrospinal fluid sample, a saliva sample and an urine sample or an extract of any of the aforementioned samples. Preferably, the sample is a blood sample, most preferably a serum sample or a plasma sample.

As mentioned herein in the context of proteins or peptides, the term "fragment" refers to smaller proteins or peptides derivable from larger proteins or peptides, which hence comprise a partial sequence of the larger protein or peptide. Said fragments are derivable from the larger proteins or peptides by saponification of one or more of its peptide bonds.

Procalcitonin in the context of the present invention preferably relates to a peptide spanning amino acid residues 1-116, 2-116, or 3-116 or fragments thereof. Thus the length of procalcitonin fragments is at least 12 amino acids, preferably more than 50 amino acids, more preferably more than 110 amino acids. PCT may comprise posttranslational modifications such as glycosylation, liposidation or derivatisation. PCT itself is a precursor of calcitonin and katacalcin. The amino acid sequence of PCT 1-116 is given in SEQ ID NO:1.

"Diagnosis" in the context of the present invention relates to the recognition and (early) detection of a bacterial infection in a subject and may also comprise differential diagnosis.

The sensitivity and specificity of a diagnostic test depends on more than just the analytical "quality" of the test, they also depend on the definition of what constitutes an abnormal result. In practice, Receiver Operating Characteristic curves (ROC curves), are typically calculated by plotting the value of a variable versus its relative frequency in "normal" (i.e. apparently healthy) and "disease" populations (i.e. patients suffering from an infection). Depending on the particular diagnostic question to be addressed, the reference group must not be necessarily "normals", but it might be a group of patients suffering from another disease or condition, from which the diseased group of interest shall be differentiated. For any particular marker, a distribution of marker levels for subjects with and without a disease will likely overlap. Under such conditions, a test does not absolutely distinguish normal from disease with 100% accuracy, and the area of overlap indicates where the test cannot distinguish normal from disease. A threshold is selected, above which (or below which, depending on how a marker changes with the disease) the test is considered to be abnormal and below which the test is considered to be normal. The area under the ROC curve is a measure of the probability that the perceived measurement will allow correct identification of a condition. ROC curves can be used even when test results don't necessarily give an accurate number. As long as one can rank results, one can create a ROC curve. For example, results of a test on "disease" samples might be ranked according to degree (e.g. 1=low, 2=normal, and 3=high). This ranking can be correlated to results in the "normal" population, and a ROC curve created. These methods are well known in the art (See, e.g., Hanley et al. 1982. *Radiology* 143: 29-36). Preferably, a threshold is selected to provide a ROC curve area of greater than about 0.5, more preferably greater than about 0.7. The term "about" in this context refers to +/−5% of a given measurement.

The horizontal axis of the ROC curve represents (1-specificity), which increases with the rate of false positives. The vertical axis of the curve represents sensitivity, which increases with the rate of true positives. Thus, for a particular cut-off selected, the value of (1-specificity) may be determined, and a corresponding sensitivity may be obtained. The area under the ROC curve is a measure of the probability that the measured marker level will allow correct identification of a disease or condition. Thus, the area under the ROC curve can be used to determine the effectiveness of the test.

According to the method, the patient is diagnosed with having a bacterial infection when said determined PCT level is higher than a predetermined threshold level. Preferably, the predetermined threshold level is between 0.02 and 0.5 ng/mL, more preferably between 0.02 ng/mL and 0.25 ng/mL, even more preferred between 0.02 ng/mL and 0.1 ng/mL, even more preferred between 0.02 ng/mL and 0.06 ng/mL, most preferred between 0.02 ng/mL and (below) 0.05 ng/mL. In a preferred embodiment the patient is diagnosed with having a bacterial infection when said determined PCT level is higher than 0.1 ng/mL, preferably higher than 0.05 ng/mL, more preferably higher than 0.025 ng/mL.

These values have been determined with a PCT test format (BRAHMS PCT LIA sensitive), which has the same calibration in the quantitative measuring range as an automated PCT Assay (BRAHMS KRYPTOR PCT sensitive). The BRAHMS PCT LIA sensitive is able to quantitatively determine PCT levels in the normal population, giving median PCT levels as described in EP 09011073.5 ("Procalcitonin for the prognosis of adverse events in the asymptomatic population"). The above mentioned values might be different in other PCT assays, if these have been calibrated differently from BRAHMS PCT LIA sensitive. The above mentioned values shall apply for such differently calibrated PCT assays accordingly, taking into account the differences in calibration. One possibility of quantifying the difference in calibration is a method comparison analysis (correlation) of the PCT assay in question with the BRAHMS PCT LIA sensitive by measuring PCT in samples using both methods. Another possibility is to determine with the PCT assay in question, given this test has sufficient analytical sensitivity, the median PCT level of a representative normal population, compare results with the median PCT levels as described in EP 09011073.5 ("Procalcitonin for the prognosis of adverse events in the asymptomatic population") and recalculate the calibration based on the difference obtained by this comparison.

Determining the level of PCT or a fragment or a precursor or fragment thereof herein is performed using a detection method and/or a diagnostic assay.

As mentioned herein, an "assay" or "diagnostic assay" can be of any type applied in the field of diagnostics. Such an assay may be based on the binding of an analyte to be detected to one or more capture probes with a certain affinity. Concerning the interaction between capture molecules and target molecules or molecules of interest, the affinity constant is preferably greater than $10^8$ $M^{-1}$.

In the context of the present invention, "capture molecules" are molecules which may be used to bind target molecules or molecules of interest, i.e. analytes (i.e. in the context of the present invention the cardiovascular peptide(s)), from a sample. Capture molecules must thus be shaped adequately, both spatially and in terms of surface features, such as surface charge, hydrophobicity, hydrophilicity, presence or absence of lewis donors and/or acceptors, to specifically bind the target molecules or molecules of interest. Hereby, the binding may for instance be mediated by ionic, van-der-Waals, pi-pi, sigma-pi, hydrophobic or hydrogen bond interactions or a combination of two or more of the aforementioned interactions between the capture molecules and the target molecules or molecules of interest. In the context of the present invention, capture molecules may for instance be selected from the group comprising a nucleic acid molecule, a carbohydrate molecule, a RNA molecule, a protein, an antibody, a peptide or a glycoprotein. Preferably, the capture molecules are antibodies, including fragments thereof with sufficient affinity to a target or molecule of interest, and including recombinant antibodies or recombinant antibody fragments, as well as chemically and/or biochemically modified derivatives of said antibodies or fragments derived from the variant chain with a length of at least 12 amino acids thereof.

The preferred detection methods comprise immunoassays in various formats such as for instance radioimmunoassay (RIA), chemiluminescence- and fluorescence-immunoassays, Enzyme-linked immunoassays (ELISA), Luminexbased bead arrays, protein microarray assays, and rapid test formats such as for instance immunochromatographic strip tests.

The assays can be homogenous or heterogeneous assays, competitive and non-competitive assays. In a particularly preferred embodiment, the assay is in the form of a sandwich assay, which is a non-competitive immunoassay, wherein the molecule to be detected and/or quantified is bound to a first antibody and to a second antibody. The first antibody may be bound to a solid phase, e.g. a bead, a surface of a well or other container, a chip or a strip, and the second antibody is an antibody which is labeled, e.g. with a dye, with a radioisotope, or a reactive or catalytically active moiety. The amount of labeled antibody bound to the analyte is then measured by an appropriate method. The general composition and procedures involved with "sandwich assays" are well-established and known to the skilled person (*The Immunoassay Handbook*, Ed. David Wild, Elsevier LTD, Oxford; 3rd ed. (May 2005), ISBN-13: 978-0080445267; Hultschig C et al., *Curr Opin Chem Biol.* 2006 Feb.; 10(1):4-10. PMID: 16376134, incorporated herein by reference).

In a particularly preferred embodiment the assay comprises two capture molecules, preferably antibodies which are both present as dispersions in a liquid reaction mixture, wherein a first labeling component is attached to the first capture molecule, wherein said first labeling component is part of a labeling system based on fluorescence- or chemiluminescence-quenching or amplification, and a second labeling component of said marking system is attached to the second capture molecule, so that upon binding of both capture molecules to the analyte a measurable signal is generated that allows for the detection of the formed sandwich complexes in the solution comprising the sample.

Even more preferred, said labeling system comprises rare earth cryptates or rare earth chelates in combination with fluorescence dye or chemiluminescence dye, in particular a dye of the cyanine type.

In the context of the present invention, fluorescence based assays comprise the use of dyes, which may for instance be selected from the group comprising FAM (5- or 6-carboxyfluorescein), VIC, NED, Fluorescein, Fluoresceinisothiocyanate (FITC), IRD-700/800, Cyanine dyes, such as CY3, CY5, CY3.5, CY5.5, Cy7, Xanthen, 6-Carboxy-2',4', 7',4,7-hexachlorofluorescein (HEX), TET, 6-Carboxy-4',5'-dichloro-2',7'-dimethody-fluorescein (JOE), N,N,N',N'-Tetramethyl-6-carboxyrhodamine (TAMRA), 6-Carboxy-X-rhodamine (ROX), 5-Carboxyrhodamine-6G (R6G5), 6-carboxyrhodamine-6G (RG6), Rhodamine, Rhodamine Green, Rhodamine Red, Rhodamine 110, BODIPY dyes, such as BODIPY TMR, Oregon Green, Coumarines such as Umbelliferone, Benzimides, such as Hoechst 33258; Phenanthridines, such as Texas Red, Yakima Yellow, Alexa Fluor, PET, Ethidiumbromide, Acridinium dyes, Carbazol dyes, Phenoxazine dyes, Porphyrine dyes, Polymethin dyes, and the like. In the context of the present invention, chemiluminescence based assays comprise the use of dyes, based on the physical principles described for chemiluminescent materials in Kirk-Othmer, Encyclopedia of chemical technology, 4th ed., executive editor, J. I. Kroschwitz; editor, M. Howe-Grant, John Wiley & Sons, 1993, vol. 15, p. 518-562, incorporated herein by reference, including citations on pages 551-562. Preferred chemiluminescent dyes are acridiniumesters.

The bacterial infection that might be diagnosed with the method of the invention can be treated with a suitable antibiotic, as known to a person of skill in the art. Possible classes of antibiotics are selected from the group consisting of penicillin (e.g. flucloxacillin, amoxicillin, ampicillin, mezlocillin), cephalosporine (e.g. cefazolin, cefuroxim, cefotaxim, cefaclor, cefalexin), β-lactamase inhibitor (e.g. sulbactam, tazobactam), tetracycline (e.g. doxycyclin, minocyclin, tetracyclin, oxytetracyclin), aminoglycoside (e.g. gentamicin, neomycin, streptomycin), makrolid antibiotics (e.g. azithromycin, clarithromycin, erythromycin, roxithromycin, spiramycin, clindamycin), lincosamide (e.g. lincomycin), gyrase inhibitor (e.g. ciprofloxacin, ofloxacin, norfloxacin), sulfonamides, trimethoprim, glycopeptide antibiotics (e.g. vancomycin), polypeptide antibiotics (e.g. colistin, polymyxin), and amphenicole (e.g. chloramphenicol).

Furthermore, the invention pertains to the use of a kit comprising one or more antibodies directed against PCT or a fragment thereof or against a PCT precursor or fragment thereof for the diagnosis of a bacterial infection in patients with non-specific complaints.

EXAMPLES

Any patients presenting with recent external laboratory results or specific ECG changes on admission (e.g. STEMI) were not eligible. Similarly, patients with known terminal medical conditions (e.g. end-stage cancer) who were admitted to the ED were not eligible. Patients were excluded if they were hemodynamically unstable or if the vital parameters were markedly outside the normal range (e.g. systolic blood pressure <90 mmHg, heart rate >120/min, body temperature >38.4 or <35.6 degrees Celsius, respiratory rate >30/min).

Diagnosis of Infection

A total of 415 patients were included into the study. 86 out of these 415 patients were diagnosed to suffer from a bacterial infection (n=19 pneumonia, n=17 cystitis, n=8 urinary tract infections, n=7 sepsis, n=10 urosepsis, n=1 septic shock, n=3 bronchitis, n=9 infection of unknown localization, n=1 peritonitis, n=1 osteomyelitis, n=1 sigmadiverculitis, n=1 colitis, n=2 COPD with acute exacerbation, n=1 cholangitis, n=1 cholecystitis, n=2 erysipel and n=2 gastroenteritis).

The diagnosis of infections in this study was carried out according to standard criteria: temperature >37.5° C., white blood cell count >11 000/mL or <4000/mL, pulmonary infiltrate on chest x-rays, or cultures positive for a pathogen.

As above outlined 86 out of these 415 patients were diagnosed to suffer from a bacterial infection (e.g. LRTI, urinary tract infections, sepsis, septic shock). Lower respiratory tract infections (LRTI) include acute bronchitis, acute exacerbations of chronic obstructive pulmonary disease (COPD) and pneumonia. Patients with LRTI exhibit at least one respiratory symptom selected from the group comprising cough, sputum production, dyspnea, tachypnea and pleuritic pain; and in addition at least one finding during auscultation (rales, crepitation) or one sign of infection (core body temperature >38° C., shivering, leukocyte count >10 G/l or <4 G/l cells). Diagnosis of urinary tract infection (UTI) was based on two of the following criteria: fever (>38° C.), urine sample positive for nitrite, leucocyturia, and significant bacteriuria. Sepsis, severe sepsis and septic shock were defined according to standard criteria (Levy, et al: 2001 SCCM/ESICM/ACCP/ATS/SIS International Sepsis Definitions Conference. Crit Care Med 2003; 31:1250-1256) . . . .

Measurement of PCT

PCT was measured using an ultrasensitive commercially available test system with a functional assay sensitivity of 0.007 ng/mL as described in Morgenthaler et al. (Morgenthaler et al. 2002. *Clin Chem* 48:788-790). Briefly, sheep antibodies were raised against the calcitonin moiety of PCT, and a mouse monoclonal antibody was raised against the katacalcin moiety of PCT. Tubes were coated with the anti-Katacalcin antibody. The anti-Calcitonin antibody was labelled with MACN Acridiniumester (InVent GmbH, Hennigsdorf, Germany) and served as tracer. Dilutions of recombinant PCT in normal horse serum were used as calibrators. 100 µL sample or standard was incubated in the coated tubes for 30 minutes, 200 µL tracer was added. After further incubation for 2 h the tubes were washed 4 times with 1 mL of LIA wash solution (BRAHMS AG, Hennigsdorf, Germany), and bound chemiluminescence was measured using a LB952T luminometer (Berthold, Wildbad, Germany).

Results

Figure 1:
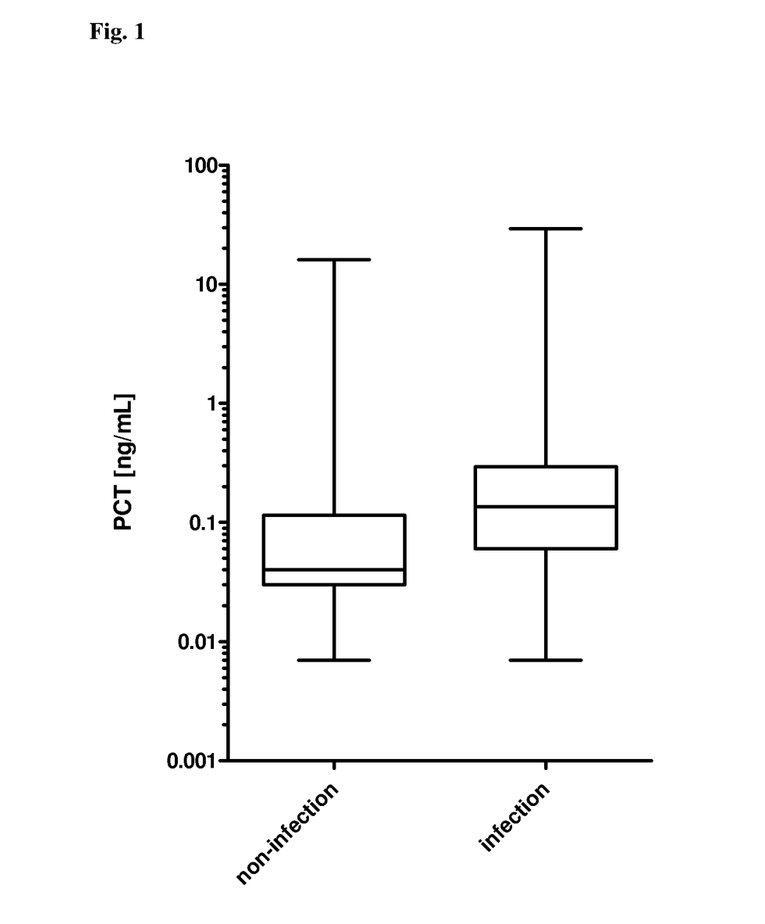
FIG. 1: PCT concentrations (on admission) of patients presenting to the ED with non-specific complaints with and without infection.
Figure 2:
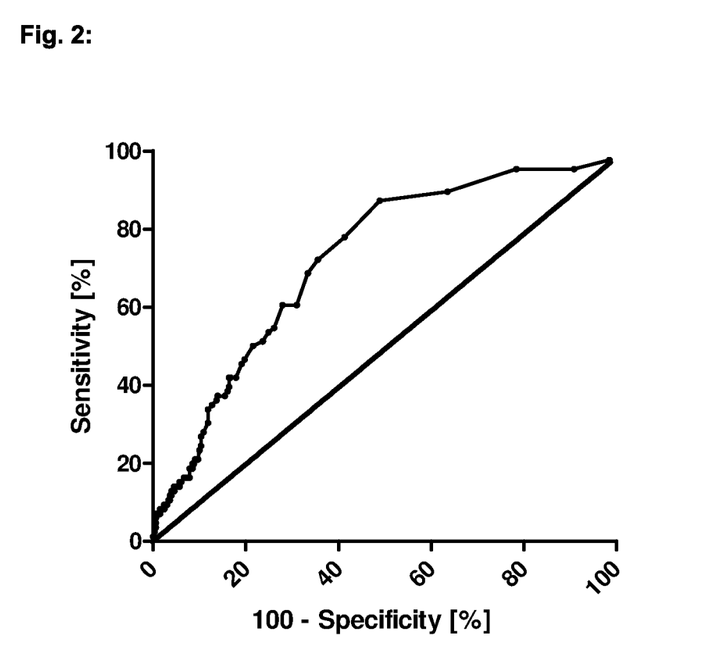
FIG. 2: ROC plot for the diagnosis of bacterial infections in patients presenting to the ED with non-specific complaints.

A total of 415 patients were included into the study. The level of procalcitonin was determined in plasma samples of patients with non-specific complaints immediately after presentation to the emergency department. 86 out of these 415 patients were diagnosed of suffering from a bacterial infection. PCT concentrations for patients with non-specific complaints with and without a bacterial infection are shown in FIG. 1. The PCT concentrations were significantly higher in patients with compared to patients without a bacterial infection ($p<0.0001$). ROC plot analysis revealed an area under curve (AUC) of 0.721 ($p<0.0001$) (FIG. 2). Different cut-off values were used to determine the corresponding sensitivity and specificity (Table 1).

to the PCT analyte to form a detectable PCT analyte: capture molecule complex, and detecting the complex, wherein said patient does not have a primary disease other than an infection, and wherein said patient is admitted to an emergency department and is judged by a physician to display one or more non-specific complaints, said non-specific complaints selected from the group consisting of: not feeling well, feeling weak, feeling exhausted, being tired or sleepy, feeling dizzy, being unable to cope with usual daily activities, and the patient being unable to recall why they were sent to the emergency department; and with the proviso that the patient does not display any symptom or condition specific to bacterial infection, said symptom or condition selected from the group consisting of headaches; pain that is in a specific part of the body; fever (>38° C.); localized redness; swelling; nausea with vomiting; local pain;

systolic blood pressure <90 mm Hg; a heart rate of >120/min; a low body temperature <35.6° C.; a respiratory rate >30/min; shaking and chills; a respiratory symptom selected from the group consisting of cough, excess sputum production, dyspnea, tachypnea and pleuritic pain; an abnormal finding during auscultation; a symptom of an infection of an organ or organ system

The invention claimed is:

1. A method for diagnosing and treating a bacterial infection, which bacterial infection is one treatable with an antibiotic, in a patient comprising the steps of:
   detecting and quantifying the level of a Procalcitonin (PCT), or a fragment thereof having at least 12 amino acids (collectively, PCT analyte) in a bodily fluid sample from said patient,
   wherein the detection and quantitation comprises a PCT detection assay with a functional assay sensitivity of below 0.06 ng/mL, comprising contacting said PCT analyte with a capture molecule that specifically binds
   selected from the group consisting of respiratory tract infection, digestive tract infections, vaginal infection, meningitis, sepsis, erysipelas, peritonitis, cholangitis, cholecystitis and osteomyelitis;
   determining a PCT analyte level higher than a predetermined threshold level of 0.02 ng/mL in said sample from said patient indicating a bacterial infection; and
   administering an antibiotic treatment to said patient upon determining the PCT analyte level is higher than the predetermined threshold indicating a bacterial infection.

2. The method of claim 1, wherein the predetermined threshold level is 0.06 ng/mL.

3. The method of claim 1, wherein the predetermined threshold level is 0.05 ng/mL.

4. The method of claim 1, wherein the predetermined threshold level is 0.1 ng/mL.

5. The method of claim 1, wherein said sample is blood, serum, plasma, cerebrospinal fluid, urine, saliva or a pleural effusion.

6. The method according to claim 1, wherein said bacterial infection to be diagnosed and treated is selected from the group consisting of a lower respiratory tract infection, infection, urinary tract infection, vaginal infection, sepsis, severe sepsis, septic shock, digestive tract infection, peritonitis, cystitis, colitis, bacterial meningitis, sinusitis, pharyngitis, cholangitis, cholecystitis, osteomyelitis, erysipelas, peritonitis, cholangitis, cholecystitis, and osteomylitis.

\* \* \* \* \*